United States Patent [19]
Hughes et al.

[11] Patent Number: 6,004,538
[45] Date of Patent: *Dec. 21, 1999

[54] ORAL COMPOSITIONS

[75] Inventors: Iain Allan Hughes, Weybridge; Mark Ieuan Edwards, Sunbury-on-Thames, both of United Kingdom

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/945,621

[22] PCT Filed: Mar. 20, 1996

[86] PCT No.: PCT/US96/03937

§ 371 Date: Oct. 28, 1997

§ 102(e) Date: Oct. 28, 1997

[87] PCT Pub. No.: WO96/33693

PCT Pub. Date: Oct. 31, 1996

[30] Foreign Application Priority Data

Apr. 28, 1995 [GB] United Kingdom ............... 9508709

[51] Int. Cl.$^6$ .............. A61K 7/16; A61K 9/20; A61K 9/68

[52] U.S. Cl. .............. 424/49; 424/48; 424/435; 424/440

[58] Field of Search .................... 424/48–58

[56] References Cited

U.S. PATENT DOCUMENTS

| | | | |
|---|---|---|---|
| 4,161,518 | 7/1979 | Wen et al. | 424/52 |
| 4,421,769 | 12/1983 | Dixon et al. | 424/358 |
| 4,511,486 | 4/1985 | Shah | 252/90 |
| 4,557,691 | 12/1985 | Martin et al. | 433/199.1 |
| 4,698,178 | 10/1987 | Huttinger et al. | 252/309 |
| 4,701,223 | 10/1987 | Eoga | 134/2 |
| 4,720,353 | 1/1988 | Bell | 252/309 |
| 4,807,649 | 2/1989 | Eoga | 134/2 |
| 4,973,412 | 11/1990 | Schmidt | 512/4 |
| 5,073,365 | 12/1991 | Katz et al. | 424/489 |
| 5,154,915 | 10/1992 | Weber et al. | 424/54 |
| 5,162,378 | 11/1992 | Guthauser | 514/785 |
| 5,188,822 | 2/1993 | Viccaro et al. | 424/52 |
| 5,266,304 | 11/1993 | Baffelli et al. | 424/49 |
| 5,427,770 | 6/1995 | Viccaro et al. | 424/54 |
| 5,527,530 | 6/1996 | Simmon et al. | 424/401 |
| 5,585,343 | 12/1996 | McGee et al. | 512/1 |
| 5,665,368 | 9/1997 | Lentini et al. | 424/401 |
| 5,759,523 | 6/1998 | Hughes et al. | 424/53 |
| 5,827,505 | 10/1998 | Hughes et al. | 424/49 |
| 5,843,881 | 12/1998 | Dubois et al. | 512/1 |
| 5,851,539 | 12/1998 | Mellul et al. | 424/405 |
| 5,856,282 | 1/1999 | Hughes et al. | 510/117 |

Primary Examiner—Shep K. Rose
Attorney, Agent, or Firm—Nick G. Clemo; Betty J. Zea

[57] ABSTRACT

An oral composition in the form of a toothpaste, powder, liquid dentifrice, mouthwash, denture cleaner, chewing gum, or candy comprising one or more oral composition components selected from abrasives, binders, humectants, surfactants, fluoride ion sources, anticalculus agents and sweetners and additionally comprising: a dimethicone copolyol selected from alkyl- and alkoxy-dimethicone copolyols having formula (I).

15 Claims, No Drawings

ORAL COMPOSITIONS

This is a 371 of PCT/US96/03937 filed Mar. 20, 1996 claiming priority of Great Britain 95 08709.4 filed Apr. 28, 1995.

TECHNICAL FIELD

The present invention relates to oral compositions such as toothpastes, toothpowders, liquid dentifrices, mouthwashes, denture cleansers, chewing gums, candies and the like. In particular, the invention relates to oral compositions having enhanced antiplaque activity together with excellent cleansing performance, physical characteristics, and in-use performance characteristics.

BACKGROUND

Plaque is initiated when bacteria adhered to pellicle form a proteinaceous film on the surface of teeth. The adherent bacteria metabolize dietary constituents and reproduce and aggregate to form the tenacious deposit known as plaque. Plaque generally consists of bacteria, bacterial end products such as polysaccharides, inorganic salts and salivary proteins. Plaque bacteria ferment dietary carbohydrates to organic acids which demineralize enamel resulting in tooth decay.

Calculus is essentially plaque that has been mineralized with calcium phosphates salts. As calculus matures and hardens, it tends to stain noticeably due to adsorption of dietary chromagens. In addition to their unattractive appearance, calculus deposits at the gum line are a contributing source of gingivitis and periodontal disease. Besides the hygienic and health problems resulting from plaque, research has shown that the primary source of bad breath is the retention and subsequent degradation of dead cellular material sloughed off continuously by the normal, healthy mouth.

Modern dental hygiene and denture preparations typically contain antiplaque and/or antitartar agents, as well as antimicrobial agents and flavorants. Antimicrobial action could affect plaque formation by either reducing the number of bacteria in the mouth/dentures or by killing those bacteria trapped in the film to prevent further growth and metabolism. Flavorants may alleviate the problem of bad breath via a deodorizing action. Some antimicrobial agents, e.g. menthol may, also serve as breath deodorizers. However, the efficacy of antimicrobial agents depends largely on their intraoral/denture retention, particularly their retention on the surface of the teeth or dentures where plaque is formed.

A typical disadvantage of known dental preparations is that only a relatively short time during which the teeth are being cleaned or the mouth is being rinsed is available for antimicrobial agents in the preparations to take effect. The problem is compounded by the fact that dentifrice preparations are used infrequently: most are used once or, perhaps, twice daily. Consequently, the long time period between brushings for a majority of the population provides optimum plaque forming conditions.

There has been a need, therefore, for developing an oral formulation which has a prolonged, residual antimicrobial and/or flavor impact effect.

It is known to include silicones in dentifrice compositions, allegedly to coat the teeth and prevent cavities and staining. For instance, GB-A689,679 discloses a mouthwash containing an organopolysiloxane for preventing adhesion of, or for removing tars, stains, tartar and food particles from the teeth. The mouthwash may include antiseptic compounds, such as thymol, and flavoring and perfuming agents.

U.S. Pat. No. 2,806,814 discloses dental preparations inducing, in combination, a higher aliphatic acyl amide of an amino carboxylic acid compound as an active and a silicone compound. The patent notes that silicone compounds have been proposed for prevention of adhesion or to facilitate the removal of tars, stains, tartar and the like from teeth. The silicone compound is said to act as a synergist in improving the antibacterial and acid inhibiting activity of the active ingredient. Dimethyl polysiloxanes are said to be particularly effective. Flavoring oils and/or menthol may be included.

U.S. Pat. No. 3,624,120 discloses quaternary ammonium salts of cyclic siloxane polymers for use as cationic surfactants, bactericides and as anticariogenic agents.

Accordingly, the present invention provides oral compositions, comprising a demethicone copolyol, having improved efficacy on plaque, mucilaginous and bacterial deposits and which at the same time provides excellent cleansing performance, physical characteristics, and in-use performance characteristics.

Oral compositions, if not aqueous themselves, are required to act within an aqueous environment. Many ingredients of such compositions act more effectively if they can first be effectively dispersed within an aqueous medium. Once dispersed, those ingredients which at by depositing on the teeth or other surfaces within, or for use within, the mouth, are then required to be deposited from aqueous dispersion in effective amounts.

Thus, the invention further provides oral compositions containing a surface active agent chosen to enhance the dispersion of the dimethicone copolyol, whilst also allowing improved substantivity, impact arid/or efficacy on teeth, gums and dentures.

SUMMARY OF THE INVENTION

According to a first aspect of the invention, there is provided an oral composition in the form of a toothpaste, powder, liquid dentifrice, mouthwash, denture cleanser, chewing gum or candy comprising one or more oral composition components selected from abrasives, binders, humectants, surfactants, fluoride ion sources, anti-calculus agents and sweeteners and additionally comprising:

i) a dimethicone copolyol selected from alkyl- and alkoxy-dimethicone copolyols having the formula (I):

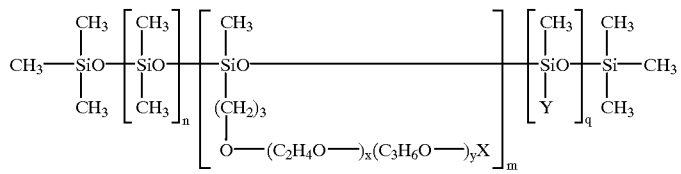

wherein X is selected from hydrogen, alkyl, alkoxy and acyl groups having from about 1 to about 16 carbon atoms, Y is selected from alkyl and alkoxy groups having from about 8 to about 22 carbon atoms, n is from about 0 to about 200, m is from about 1 to about 40, q is from about 1 to about 100, the molecular weight of the residue $(C_2H_4O—)_x—(C_3H_6O—)_yX$ is from about 50 to about 2000, preferably from about 250 to about 1000 and x and y are such that the weight ratio of oxyethylene:oxypropylene is from about 100:0 to about 0:100, preferably from about 100:0 to about 20:80; and ii) a silicone surfactant having the general formula (I) wherein X is selected from hydrogen, alkyl, alkoxy and acyl groups having from about 1 to about 16 carbon atoms, Y is $CH_3$, q is 0, n is from about 1 to about 100, m is from about 1 to about 40, the molecular weight of the residue $(C_2H_4O—)_x(C_3H_6O—)_yX$ is from about 50. to about 2000, and x and y are such that the weight ratio of oxyethylene:oxypropylene is from about 100:0 to about 0:100.

All percentages and ratios herein are by weight of total composition, unless otherwise indicated.

DETAILED DESCRIPTION OF THE INVENTION

The oral compositions of the invention thus comprise a dimethicone copolyol antiplaque agent and a dimethicone copolyol surfactant, while preferred compositions additionally comprise a lipophilic compound and/or one or more oral composition components selected from abrasives, binders, humectants, surfactants, fluoride ion sources, anti-calculus agents and sweeteners. Each of these will be discussed in turn.

In general terms, the dimethicone copolyol antiplaque agent is selected from alkyl- and alkoxy-dimethicone copolyols having the formula (I):

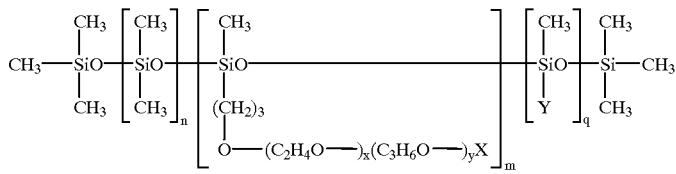

wherein X is selected from hydrogen, alkyl, alkoxy and acyl groups having from about 1 to about 16 carbon atoms, Y is selected from alkyl and alkoxy groups having from about 8 to about 22 carbon atoms, n is from about 0 to about 200, m is from about 1 to about 40, q is from about 1 to about 100, the molecular weight of the residue $(C_2H_4O—)_x(C_3H_6O—)_yX$ is from about 50 to about 2000, preferably from about 250 to about 1000 and x and y are such that the weight ratio of oxyethylene:oxypropylene is from about 100:0 to about 0:100, preferably from about 100:0 to about 20:80.

In preferred embodiments, the dimethicone copolyol is selected from $C_{12}$ to $C_{20}$ alkyl dimethicone copolyols and mixtures thereof. Highly preferred is cetyl dimethicone copolyol marketed under the Trade Name Abil EM90. The dimethicone copolyol is generally present in a level of from about 0.01% to about 25%, preferably from about 0.1% to about 5%, more preferably from about 0.5% to about 1.5% by weight.

A second essential ingredient of the oral compositions of the invention is a silicone surfactant having the general formula (I) wherein X is selected from hydrogen, alkyl, alkoxy and acyl groups having from about 1 to about 16 carbon atoms, Y is $CH_3$, q is 0, n is from about 1 to about 100, m is from about 1 to about 40, the molecular weight of the residue $(C_2H_4O—)_x—(C_3H_6O—)_yX$ is from about 50 to about 2000, and x and y are such that the weight ratio of oxyethylene:oxypropylene is from about 100:0 to about 0:100.

The silicone surfactant, itself a dimethicone copolyol, assists in dispersing the dimethicone copolyol antiplaque agent in aqueous media whilst still allowing the copolyol antiplaque agent to deposit onto surfaces such as teeth, gums or artificial dentures. In preferred embodiments, the silicone surfactant is selected from dimethicone copolyols having a HLB value of greater than 14 and mixtures thereof. Highly preferred are end-capped (X is alkyl, more particularly methyl) dimethicone copolyols, especially where the pendant side chain is all oxyethylene (y is 0), such as that marketed under the Trade Name Silwet L7600. The silicone surfactant is generally present in a level of from about 0.01% to about 25%, preferably from about 0.3% to about 10%, more preferably from about 0.5% to about 5% by weight. It will be appreciated that the precise amount will depend on the amount of the dimethicone copolyol antiplaque agent used. In general the ratio of silicone surfactant to dimethicone copolyol antiplaque agent will be from about 0.5:1 to 15:1, more preferably from about 1:1 to 10:1, most preferably from about 2:1 to 8:1 by weight.

The oral compositions of the invention preferably also include a lipophilic compound. In general terms, lipophilic compounds suitable for use herein are oil-like materials which are soluble or solubilisable in the dimethicone copolyol, preferably at a level of at least about 1%, more preferably at least about 5% by weight at 25° C. Preferred lipophilic compounds are selected from flavorants, physiological cooling agents and antimicrobial compounds. The dimethicone copolyol acts to enhance the substantivity of the lipophilic compound to teeth and/or dentures, thereby providing enhanced and/or sustained flavor impact and antimicrobial efficacy.

Lipophilic flavorants suitable for use herein comprise one or more flavor components selected from wintergreen oil, oregano oil, bay leaf oil, peppermint oil, spearmint oil, clove oil, sage oil, sassafras oil, lemon oil, orange oil, anise oil, benzaldehyde, bitter almond oil, camphor, cedar leaf oil, marjoram oil, citronella oil, lavendar oil, mustard oil, pine oil, pine needle oil, rosemary oil, thyme oil, cinnamon leaf oil, and mixtures thereof.

Lipophilic antimicrobial compounds suitable for use herein include thymol menthol, triclosan, 4-hexylresorcinol, phenol, eucalyptol, benzoic acid, benzoyl peroxide, butyl paraben, methyl paraben, propyl paraben, salicylamides, and mixtures thereof.

Physiological cooling agent suitable for use herein include carboxamides, menthane esters and menthane ethers, and mixtures thereof.

Suitable menthane ethers for use herein are selected from those with the formula:

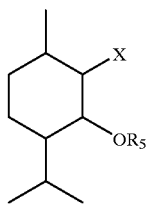

where $R_5$ is an optionally hydroxy substituted aliphatic radical containing up to 25 carbon atoms, preferably up to 5 carbon atoms, and where X is hydrogen or hydroxy, such as those commercially available under the trade name Takasago, from Takasago International Corporation. A particularly preferred cooling agent for use in the compositions of the present invention is Takasago 10 [3-1-menthoxy propan-1,2-diol (MPD)]. MPD is a monoglycerin derivative of 1-menthol and has excellent cooling activity.

The carboxamides found most useful are those described in U.S. Pat. No. 4,136,163, Jan. 23, 1979 to Wason et al., and U.S. Pat. No. 4,230,688, Oct. 28, 1980 to Rawsell et al.

The level of lipophilic compound in the compositions of the invention is generally in the range from about 0.01% to about 10%, preferably from about 0.05% to about 5%, more preferably from about 0.1% to about 3% by weight.

Compositions in the form of toothpastes, denture cleansing liquids and pastes and the like will generally comprise a binder or thickening agent. Binders suitable for use herein include carboxyvinyl polymers, carrrageenan, hydroxyethyl cellulose and water soluble salts of cellulose ethers such as sodium carboxymethyl cellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. Binders/thickening agents can be used in an amount from about 0.1% to about 5.0%, preferably from about 0.1 to about 1% by weight of the total composition.

It is also desirable to include some humectant material in a toothpaste to keep the composition from hardening upon exposure to air. Certain humectants can also impart a desirable sweetness to toothpaste compositions. Liquid dentifrice and mouthwashes can also contain a quantity of humectant. Suitable humectants include glycerin, sorbitol, xylitol, polyethylene glycols, propylene glycol, other edible polyhydric alcohols, and mixtures thereof. When present, humectants generally represent from about 10% to about 70%, by weight of the compositions of the invention.

Toothpastes, liquid dentifrices and denture cleansers in liquid or paste form will generally comprise an abrasive polishing material. The abrasive polishing material contemplated for use herein can be any material which does not excessively abrade dentin or denture acrylic. These include, for example, silicas including xerogels, hydrogels, aerogels and precipitates, calcium and magnesium carbonates, calcium ortho-, pyro- meta- and polyphosphates such as dicalcium orthophosphate dihydrate, calcium pyrophosphate, tricalcium phosphate, and calcium polymetaphosphate, insoluble sodium polymetaphosphate, alumina and hydrates thereof such as alpha alumina trihydrate, aluminosilicates such as calcined aluminium silicate and aluminium silicate, magnesium and zirconium silicates such as magnesium trisilicate and thermosetting polymerised resins such as particulate condensation products of urea and formaldehyde, polymethylmethacrylate, powdered polyethylene and others such as disclosed in U.S. Pat. No. 3,070,510, Dec. 25, 1962 Mixtures of abrasives can also be used. The abrasive polishing materials generally have an average particle size of from about 0.1 to about 30 microns, preferably from about 5 to 15 microns.

Silica dental abrasives of various types offer exceptional dental cleaning and polishing performance without unduly abrading tooth enamel or dentin. The silica abrasive can be precipitated silica or silica gels such as the silica xerogels described in Pader et al., U.S. Pat. No. 3,538,230, issued Mar. 2, 1970 and DiGiulio, U.S. Pat. No. 3,862,307, Jun. 21, 1975, for example silica xerogels marketed under the tradename "Syloid" by W. R. Grace & Company, Davison Chemical Division. Suitable precipitated silica materials include those marketed by the J. M. Huber Corporation under the tradename, "Zeodent", particularly the silica carrying the designation "Zeodent 119". These silica abrasives are described in U.S. Pat. No. 4,340,583, Jul. 29, 1982.

Highly preferred herein from the viewpoint of providing good cleansing performance combined with excellent compatibility with the antiplaque agent are calcium carbonate abrasives.

The abrasive is generally present in dentifrice formulations of the invention at a level of from about 10% to about 70%, preferably from about 15% to about 25% by weight.

The present compositions can also contain surfactants. Suitable surfactants are those which are reasonably stable and foam throughout a wide pH range, including non-soap anionic, nonionic, cationic, zwitterionic and amphoteric organic synthetic detergents. Many of these suitable agents are disclosed by Gieske et al. in U.S. Pat. No. 4,051,234, Sep. 27, 1977.

Examples of suitable surfactants include alkyl sulfates; condensation products of ethylene oxide with fatty acids, fatty alcohols, fatty amides, polyhydric alcohols (e.g. sorbitan monostearate, sorbitan oleate), alkyl phenols (e.g. Tergitol) and polypropyleneoxide or polyoxybutylene (e.g. Pluronics); amine oxides such as dimethyl cocamine oxide, dimethyl lauryl amine oxide and cocoalkyldimethyl amine oxide (Aromox); polysorbates such as Tween 40 and Tween 80 (Hercules); sorbitan stearates, sorbitan monoaleate, etc; sarcosinates such as sodium cocoylsarcosinate, sodium lauroyl sarcosinate (Hamposyl-95 ex W. R. Grace); cationic surfactants such as cetyl pyridinium chloride, cetyl trimethyl ammonium bromide, di-isobutyl phenoxy ethoxy ethyldimethyl benzyl ammonium chloride and coconut alkyl trimethyl ammonium nitrate.

A soluble fluoride ion source can also be incorporated in the present compositions. The soluble fluoride ion source is used in amounts sufficient to provide from about 50 to about 3500 ppm of the fluoride ion. Preferred fluorides are sodium fluoride, stannous fluoride, indium fluoride, zinc ammonium fluoride, tin ammonium fluoride, calcium fluoride and sodium monofluorophosphate. Norris et al., U.S. Pat. No. 2,946,735, issued Jul. 26, 1960 and Widder et al., U.S. Pat. No. 3,678,154, issued Jul. 18, 1972 disclose such salts as well as others.

The present compositions can also include an anti-calculus agent. Suitable anti-calculus agents include the di- and tetra-alkali metal pyrophosphates as set out in EP-A-097476. Specific salts include tetra alkali metal pyrophosphate, dialkali metal diacid pyrophosphate, trialiali metal monoacid pyrophosphate and mixtures thereof, wherein the alkali metals are sodium or potassium. The salts are useful in both their hydrated and unhydrated forms. The amount of pyrophosphate salt useful in these compositions is any effective amount and is generally enough to provide in composition at least 1.0% $P_2O_7^{-4}$, preferably from about 1.5% to about 10%, more preferably from about 3% to about 6% by weight or composition. The pyrophosphate salts are described in more detail in Kirk & Othmer, *Encyclopedia of Chemical Technology,* Second Edition, Volume 15, Interscience Publishers (1968).

Other anti-calculus agents suitable herein are zinc salts. Zinc salts are disclosed in U.S. Pat. No. 4,100,269, U.S. Pat. No. 4,416,867, U.S. Pat. No. 4,425,325 and U.S. Pat. No. 4,339,432. A preferred agent of the zinc variety is zinc citrate. Zinc compounds can be present in amounts sufficient to provide from about 0.01% to about 4%, preferably from about 0.05% to about 1% by weight of zinc ion.

Other suitable anti-calculus agents include the synthetic anionic polymers (including polyacrylates and copolymers of maleic anhydride or acid and methyl vinyl ether (eg Gantrez) as described in U.S. Pat. No. 4,627,977, polyamino propane sulfonic acid, polyphosphates (eg tripolyphosphate, hexametaphosphate), diphosphonates (eg EHDP, AHP), polypeptides (eg polyaspartic and polyglutamic acids), and mixtures thereof.

Sweetening agents which can be used include aspartame, acesulfame, saccharin, dextrose, levulose and sodium cyclamate. Sweetening agents are generally used at levels of from about 0.005% to about 2% by weight of composition.

Other optional components for use herein include water-soluble antibacterial agents, such as chlorhexidine digluconate, quaternary ammonium antibacterial compounds and water-soluble sources of certain metal ions such as zinc, copper, silver and stannous (e.g., zinc, copper and stannous chloride, and silver nitrate); pigments such as titanium dioxide; orally acceptable dyes/colorants such as FD&C Blue #1, FD&C Yellow #10, FD&C Red #40; antioxidants, vitamins such as vitamin C and E, other antiplaque agents such as stannous salts, copper salts, strontium salts and magnesium salts; pH adjusting agents, anticaries agents such as urea, calcium glycerophosphate, sodium trimetaphosphate, plant extracts, desensitizing agents for sensitive teeth such as potassium nitrate and potassium citrate, and mixtures thereof.

Typically, mouthwashes comprise a water/alcohol solution, flavor, humectant, sweetener, sudsing agent, and colorant as described above. Mouthwashes can include ethanol at a level of from 0 to 60%, preferably from 5 to 30% by weight.

Denture cleanser compositions of the invention can additionally include one or more bleaching agents, organic peroxyacid precursors, effervescence generators, chelating agents, etc The bleaching agent takes the form of an inorganic persalt and can be selected from any of the well-known bleaching agents known for use in denture cleansers such as the alkali metal and ammonium persulfates, perborates, percarbonates and perphosphates and the alkali metal and alkaline earth metal peroxides. Examples of suitable bleaching agents include potassium, ammonium, sodium and lithium persulfates and perborate mono- and tetrahydrates, sodium pyrophosphate peroxyhydrate and magnesium, calcium, strontium and zinc peroxides. Of these, however, the alkali metal persulfates, perborates and mixtures thereof are prefered for use herein, highly preferred being the alkali metal perborates. Indeed, it is a feature of the invention that the tablet compositions herein will provide excellent antimicrobial activity even in the absence of alkali metal persulfates.

The amount of bleaching agent in the total composition is generally from about 5 to about 70% preferably from about 10% to about 50%. In compositions comprising a mixture of alkali metal persulfates and perborates, the overall persulfate:perborate ratio is suitably from about 5:1 to about 1:5, more especially from about 2:1 to about 1:2.

The denture cleansing compositions can also incorporate an effervescence generator, ie a material which in the presence of water releases carbon dioxide or oxygen with effervescence. The effervescence generator can be selected from generators which are effective under acid, neutral or alkaline pH conditions, but preferably it consists of a combination of a generator which is effective or most effective under acid or neutral pH conditions and a generator which is effective or most effective under alkaline pH conditions. Effervescence generators which are effective under acid or neutral pH conditions include a combination of at least one alkali metal carbonate or bicarbonate, such as sodium bicarbonate, sodium carbonate, sodium sesquicarbonate, potassium carbonate, potassium bicarbonate, or mixtures thereof, in admixture with at least one non-toxic, physiologically-acceptable organic acid, such as tartaric, fumaric, citric, malic, maleic, gluconic, succinic, salicylic, adipic or sulphamic acid, sodium fumarate, sodium or potassium acid phosphates, betaine hydrochloride or mixtures thereof. Of these, malic acid is preferred. Effervescence generators which are effective under alkaline pH conditions include persalts such as alkali and alkaline earth metal peroxoborates as well as perborates, persulphates, percarbonates, perphosphates and mixtures thereof as previously described, for example, a mixture of an alkali metal perborate (anhydrous, mono- or tetrahydrate) with a monopersulphate such as Caroat® marketed by E I du Pont de Nemours Co. and which is a 2:1:1 mixture of monopersulphate, potassium sulphate and potassium bisulphate and which has an active oxygen content of about 4.5%.

In preferred denture cleansing compositions in tablet form, the effervescence generator takes the form of a solid base material which in the presence of water releases carbon dioxide or oxygen with effervescence.

Suitably, the solid base material incorporates a (bi) carbonate/acid effervescent couple optionally in combination with a perborate/persulphate oxygen effervescence generator. The combination of generators is valuable for achieving optimum dissolution characteristics and pH conditions for achieving optimum cleaning and antimicrobial activity. The (bi)carbonate components generally comprise from about 5% to about 65%, preferably from about 25% to 55% of the total composition; the acid components generally comprise from about 5% to about 50%, preferably from about 1 0% to about 30% of the total composition.

The denture cleansing compositions of the invention can be supplemented by other known components of such formulations. An especially preferred additional component is an organic peroxyacid precursor, which in general terms can be defined as a compound having a titre of at least 1.5 ml of 0.1N sodium thiosulfate in the following peracid formation test.

A test solution is prepared by dissolving the following materials in 1000 mls distilled water:

| | |
|---|---:|
| sodium pyrophosphate ($Na_4P_2O_7.10H_2O$) | 2.5 g |
| sodium perborate ($NaBO_2.H_2O_2.3H_2O$) having 10.4% available oxygen | 0.615 g |
| sodium dodecylbenzene sulphonate | 0.5 g |

To this solution at 60° C. an amount of activator is added such that for each atom of available oxygen present one molecular equivalent of activator is introduced.

The mixture obtained by addition of the activator is vigorously stirred and maintained at 60° C. After 5 minutes from addition, a 100 ml portion of the solution is withdrawn and immediately pipetted onto a mixture of 250 g cracked ice and 15 ml glacial acetic acid. Potassium iodide (0.4 g) is then added and the liberated iodine is immediately titrated with 0.1 N sodium thiosulphate with starch as indicator until the first disappearance of the blue colour. The amount of sodium thiosulphate solution used in ml is the titre of the bleach activator.

The organic peracid precursors are typically compounds containing one or more acyl groups, which are susceptible to perhydrolysis. The preferred activators are those of the N-acyl or O-acyl compound type containing a acyl radical R—CO wherein R is a hydrocarbon or substituted hydrocarbon group having preferably from about 1 to about 20 carbon atoms. Examples of suitable peracid precursors include:

1) Acyl organoamides of the formula $RCONR_1R_2$, where RCO is carboxylic acyl radical, $R_1$ is an acyl radical and $R_2$ is an organic radical, as disclosed in U.S. Pat. No. 3,117,148. Examples of compounds failing under this group include:
   a) N,N-diacetylaniline and N-acetylphthalimide;
   b) N-acylhydantoins, such as N,N'-diacetyl-5,5-dimethylhydantoin;
   c) Polyacylated alkylene diamines, such as N,N,N'N'-tetraacetylethylenediamine (TAED) and the corresponding hexamethylenediamine (TAHD) derivatives, as disclosed in GB-A-907,356, GB-A-907,357 and GB-A-907,358;
   d) Acylated glycolurils, such as tetraacetylglycoluril, as disclosed in GB-A-1,246,338, GB-A-1,246,339 and GB-A-1,247,429.

2) Acylated sulphonamides, such as N-methyl-N-benzoyl-menthane sulphonamide and N-phenyl-N-acetyl menthane sulphonamide, as disclosed in GB-A-3,183,266.

3) Carboxylic esters as disclosed in GB-A-836,988, GB-A-963,135 and GB-A-1,147,871. Examples of compounds of this type include phenyl acetate, sodium acetoxy benzene sulphonate, trichloroethylacetate, sorbitol hexaacetate, fructose pentaacetate, p-nitrobenzaldehyde diacetate, isopropeneyl acetate, acetyl aceto hydroxamic acid, and acetyl salicylic acid. Other examples are esters of a phenol or substituted phenol with an alpha-chlorinated lower aliphatic carboxylic acid, such as chloroacetylphenol and chloroacetylsalicylic acid, as disclosed in U.S. Pat. No. 3,130,165.

4) Carboxylic esters having the gernal formal Ac L wherein Ac is the acyl moiety of an organic carboxylic acid comprising an optionally substituted, linear or branched $C_6-C_{20}$ alkyl or alkenyl moiety or a $C_6-C_{20}$ alkyl-substituted aryl moiety and L is a leaving group, the conjugate acid of which has a pKa in the range from 4 to 13, for example oxybenzenesulfonate or oxybenzoate. Preferred compounds of this type are those wherein:
   a) Ac is $R_3$—CO and $R_3$ is a linear or branched alkyl group containing from 6 to 20, preferably 6 to 12, more preferably 7 to 9 carbon atoms and wherein the longest linear alkyl chain extending from and including the carbonyl carbon contains from 5 to 18, preferably 5 to 10 carbon atoms, $R_3$ optionally being substituted (preferably alpha to the carbonyl moiety) by Cl, Br, $OCH_3$ or $OC_2H_5$. Examples of this class of material include sodium 3,5,5-trimethylhexanoyloxybenzene sulfonate, sodium 3,5,5-trimethylhexanoyloxybenzoate, sodium 2-ethylhexanoyl oxybenzenesulfonate, sodium nonanoyl oxybenzene sulfonate and sodium octanoyl oxybenezenesulfonate, the acyloxy group in each instance preferably being p-substituted;
   b) Ac has the formula $R_3(AO)_mXA$ wherein $R_3$ is a linear or branched alkyl or alkylaryl group containing from 6 to 20, preferably from 6 to 15 carbon atoms in the alkyl moiety, $R_5$ being optionally substituted by Cl, Br, $OCH_3$, or $OC_2H_5$, AO is oxyethylene or oxypropylene, m is from 0 to 100, X is 0, $NR_4$ or CO—$NR_4$, and A is CO, CO—CO, $R_6$—CO, CO—$R_6$—CO, or CO—$NR_4$—$R_6$—CO wherein $R_4$ is $C_1-C_4$ alkyl and $R_6$ is alkylene, alkenylene, arylene or alkarylene containing from 1 to 8 carbon atoms in the alkylene or alkenylene moiety. Bleach activator compounds of this type include carbonic acid derivatives of the formula $R_3(AO)_mOCOL$, succinic acid derivatives of the formula $R_3OCO(CH_2)_2COL$, glycollic acid derivatives of the formula $R_3OCH_2COL$, hydroxypropionic acid derivatives of the formula $R_3OCH_2CH_2COL$, oxalic acid derivatives of the formula $R_3OCOCOL$, maleic and fumaric acid derivatives of the formula $R_3OCOCH=CHCOL$, acyl aminocaproic acid derivatives of the formula $R_3CONR_1(CH_2)_6COL$, acyl glycine derivatives of the formula $R_3CONR_1CH_2COL$, and amino-6-oxocaproic acid derivatives of the formula $R_3N(R_1)CO(CH_2)_4COL$. In the above, m is preferably from 0 to 10, and $R_3$ is preferably $C_6-C_{12}$, more preferably $C_6-C_{10}$ alkyl when m is zero and $C_9-C_{15}$ when m is non-zero. The leaving group L is as defined above.

5) Acyl-cyanurates, such as triacetyl- or tribenzoylcyanurates, as disclosed in U.S. Pat. No. 3,332,882.

6) Optionally substituted anhydrides of benzoic or phthalic acid, for example, benzoic anhydride, m-chlorobenzoic anhydride and phthalic anhydride.

Of all the above, preferred are organic peracid precursors of types 1(c) and 4(a).

Where present, the level of peroxyacid bleach precursor by weight of the total composition is preferably from about 0.1% to about 10%, more preferably from about 0.5% to about 5% and is generally added in the form of a bleach precursor agglomerate.

The bleach precursor agglomerates preferred for use herein generally comprise a binder or agglomerating agent in a level of from about 5% to about 40%, more especially from about 10% to about 30% by weight thereof. Suitable agglomerating agents include polyvinylpyrrolidone, poly (oxyethylene) of molecular weight 20,000 to 500,000, polyethyleneglycols of molecular weight of from about 1000 to about 50,000, Carbowax having a molecular weight of from 4000 to 20,000, nonionic surfactants, fatty acids, sodium carboxymethyl cellulose, gelatin, fatty alcohols, phosphates and polyphosphates, clays, aluminosilicates and polymeric polycarboxylates. Of the above, polyethyleneglycols are highly preferred, especially those having molecular weight of from about 1,000 to about 30,000, preferably 2000 to about 10,000.

Preferred from the viewpoint of optimum dissolution and pH characteristics are bleach precursor agglomerates which comprise from about 10% to about 75%, preferably from about 20% to about 60% by weight thereof of peroxyacid bleach precursor, from about 5% to about 60% preferably from about 5% to about 50%, more preferably from about 10% to about 40% of a (bi) carbonate/acid effervescent couple, from about 0% to about 20% of a peroxoboroate, and from about 5% to about 40%, preferably from about 10% to about 30% of an agglomerating agent. The final bleach precursor granules desirably have an average particle size of from about 500 to about 1500, preferably from about 500 to about 1,000 um, this being valuable from the viewpoint of optimum dissolution performance and aesthetics. The level of bleach precursor agglomerates, moreover, is preferably from about 1% to about 20%, more preferably from about 5% to about 15% by weight of composition.

The denture cleansing compositions of the invention can be in paste, tablet, granular or powder form, although tablet-form compositions are highly preferred herein. Compositions in tablet form can be single or multiple layered tablets.

Denture cleansing compositions of the invention can be supplemented by other usual components of such formulations, especially surfactants, chelating agents, enzymes, flavorants, physiological cooling agents, antimicrobial compounds, dyestuffs, sweeteners, tablet binders and fillers, foam depressants such as dimethylpolysiloxanes, foam stabilizers such as the fatty acid sugar esters, preservatives, lubricants such as talc, magnesium stearate, finely divided amorphous pyrogenic silicas, etc. The free moisture content of the final composition is desirably less than about 1% and especially less than about 0.5%.

Tablet binders and fillers suitable for use herein include polyvinylpyrrolidone, poly(oxyethylene) of molecular weight 20,000 to 500,000, polyethyleneglycols of molecular weight of from about 1 300 to about 50,000, Carbowax having a molecular weight of from 4000 to 20,000, nonionic surfactants, fatty acids, sodium carboxymethyl cellulose, gelatin, fatty alcohols, clays, polymeric polycarboxylates, sodium carbonate, calcium carbonate, calcium hydroxide, magnesium oxide, magnesium hydroxide carbonate, sodium sulfate, proteins, cellulose ethers, cellulose esters, polyvinyl alcohol, alginic acid esters, vegetable fatty materials of a pseudocolloidal character. Of the above, polyethyleneglycols are highly preferred, especially those having molecular weight of from about 1,000 to about 30,000, preferably from about 12,000 to about 30,000.

The surface active agent used in the denture cleansing compositions of the invention can be selected from the many available that are compatible with the other ingredients of the denture cleanser, both in the dry state and in solution. Such materials are believed to improve the effectiveness of the other ingredients of the composition by aiding their penetration into the interdental surfaces. Also, these materials aid in the removal of food debris attached to the teeth. Between 0.1 and 5 percent by weight of the dry composition of a dry powder or granular anionic surface active agent, such as sodium lauryl sulfate, sodium N-lauroylsarcosinate, sodium lauryl sulfoacetate or dioctyl sodium sulfosuccinate or ricinoleyl sodium sulfosuccinate, may, for example, be included in the composition and preferably the surface active agent comprises between 0.5 and 4 percent of the composition.

Suitable cationic, non-ionic and ampholytic surface active agents include, for example, quaternary ammonium compounds such as cetyltrimethylammonium bromide, condensation products of alkylene oxides such as ethylene or propylene oxide with fatty alcohols, pherols, fatty amines or fatty acid alkanolamides, the fatty acid alkanolamides themselves, esters of long-chained ($C_8$–$C_{22}$) fatty acids with polyalcohols or sugars, for example glycerylmonostearate or saccharose monolaurate or sorbitolpolyoxyethylenemono-or di-stearate, betaines, sulphobetaines or long-chain alkylaminocarboxylic acids.

Chelating agents beneficially aid cleaning and bleach stability by keeping metal ions, such as calcium, magnesium, and heavy metal cations in solution. Examples of suitable chelating agents include sodium tripolyphosphate, sodium acid pyrophosphate, tetrasodium pyrophosphate, aminopoly-carboxylates such as nitrilotriacetic acid and ethylenediamine tetracetic acid and salts thereof, and polyphosphonates and aminopolyphosphonates such as hydroxyethanediphosphonic acid, ethylenediamine tetramethylene-phosphonic acid, diethylenetriaminepentamethylenephosphonic acid and salts thereof. The chelating agent selected is not critical except that it must be compatible with the other ingredients of the denture cleanser when in the dry state and in aqueous solution. Advantageously, the chelating agent comprises between 0.1 and 60 percent by weight of the composition and preferably between 0.5 and 30 percent. Phosphonic acid chelating agents, however, preferably comprise from about 0.1 to about 1 percent, preferably from about 0.1% to about 0.5% by weight of composition.

Enzymes suitable for use herein are exemplified by proteases, alkalases, amylases, lipases, dextranases, mutanases, glucanases; etc.

The following Examples further describe and demonstrate the preferred embodiments within the scope of the present invention.

EXAMPLES I TO V

The following are representative denture cleansing tablets according to the invention. The percentages are by weight of the total tablet. The tablets are made by compressing a mixture of the granulated components in a punch and dye tabletting press at a pressure of about $10^5$ kPa.

|  | I | II | III | IV | V |
|---|---|---|---|---|---|
| Malic Acid | 12 | 10 | 12 | — | 14 |
| Citric Acid | — | 10 | — | 12 | — |
| Sodium Carbonate | 10 | 8 | 8 | 6 | 10 |
| Sulphamic Acid | 5 | — | — | 3 | 3 |
| PEG 20,000 | — | 3 | 5 | 4 | 5 |
| PVP 40,000 | 5 | 3 | — | — | — |
| Sodium Bicarbonate | 21 | 23.2 | 23.9 | 13.9 | 20 |
| Sodium Perborate Monohydrate | 15 | 12 | 13 | 27 | 14 |
| Potassium Monopersulphate | 14.4 | 16 | 11 | — | 13.5 |
| Pyrogenic Silica | 0 | 0.3 | 0.1 | 0.1 | — |
| Talc | 2 | — | — | — | — |
| EDTA | — | — | 1 | — | 3 |
| EDTMP[1] | 1 | — | — | 1 | — |
| Flavor[5] | 2 | 1 | 2 | 1 | 2 |
| Abil EM90[4] | 0.6 | 1.5 | 5 | 8 | 0.5 |
| Silwet L7600[6] | 3 | 4 | — | 12 | 5 |
| Silwet L7230[7] | — | — | 9 | — | — |
| Bleach Precursor Agglomerate |  |  |  |  |  |
| TAED[2] | 2 | — | 4 | 5 | 2.5 |
| TMHOS[3] | 2 | 3 | — | — | — |
| Sulphamic Acid | 2 | 2 | 2 | 2 | 3.5 |
| Sodium Bicarbonate | 0.5 | 0.2 | 0.2 | 0.5 | 2 |
| PEG 6000 | 2.5 | 2 | 2.4 | 2.5 | 1.5 |
| Dye | — | 0.8 | 1.4 | 2 | 0.5 |
| Total | 100 | 100 | 100 | 100 | 100 |

[1]Ethylenediaminetetramethylenephosphonic acid
[2]Tetraacetylethylene diamine
[3]Sodium 3,5,5-trimethylhexanoyloxybenzene sulfonate
[4]Cetyl dimethicone copolyol
[5]Peppermint-based flavor
[6]CAS Registry No. 68938-54-5 from Union Carbide
[7]CAS Registry No. 68937-55-3 from Union Carbide In Examples I to V above, the overall tablet weight is 3 g; diameter 25 mm.

The denture cleansing tablets of Examples I to V display improved antiplaque, cleansing and anti-bacterial activity together with excellent cohesion and other physical and in-use performance characteristics.

EXAMPLES VI TO VIII

The following are representative toothpaste/denture cleansing pastes according to the invention. The percentages are by weight of total composition.

|  | VI | VII | VIII |
|---|---|---|---|
| Calcium Carbonate | 20 | 25 | 15 |
| Glycerine | 10 | 12 | 8 |
| Sodium CMC | 3.5 | 3 | 4 |
| Titanium Dioxide | 0.7 | 0.5 | 0.6 |
| Methyl/Propyl Parabens | 0.1 | 0.1 | 0.1 |
| Sodium Saccharin | 0.3 | 0.4 | 0.2 |
| Flavor[5] | 1 | 1 | 2 |
| Abil EM90[4] | 1 | 1.5 | 0.3 |
| Silwet L7600[6] | 3 | 2.5 | 2 |
| Trictosan | — | 0.5 | — |
| Water |  | To 100% |  |

The toothpastes/denture cleansing pastes of Examples VI to VIII display improved antiplaque, flavor impact and anti-bacterial activity together with excellent cleansing characteristics.

What is claimed is:

1. An oral composition in the form of a toothpaste, powder, liquid dentifrice, mouthwash, denture cleanser, chewing gum or candy comprising one or more oral composition components selected from the group consisting of abrasives, binders, humectants, surfactants, fluoride ion sources, anti-calculus agents and sweeteners and additionally comprising:

i) a dimethicone copolyol selected from alkyl- and alkoxy-dimethicone copolyols having the formula (I):

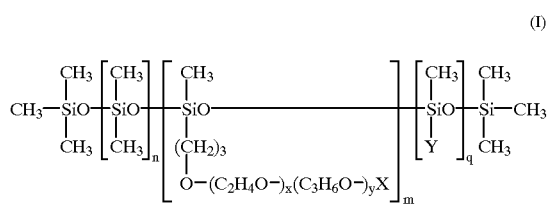

(I)

wherein X is selected from the group consisting of hydrogen, alkyl, alkoxy and acyl groups having from about 1 to about 16 carbon atoms, Y is selected from the group consisting of alkyl and alkoxy groups having from about 8 to about 22 carbon atoms, n is from about 0 to about 200, m is from about 1 to about 40, q is from about 1 to about 100, the molecular weight of the residue $(C_2H_4O-)_x-(C_3H_6O-)_yX$ is from about 50 to about 2000 and x and y are such that the weight ratio of oxyethylene:oxypropylene is from about 100:1 to about 0:100; and ii) a silicone surfactant having the general formula (I) wherein x is selected from the group consisting of hydrogen, alkyl, alkoxy and acyl groups having from about 1 to about 16 carbon atoms, Y is $CH_3$, q is 0, n is from about 1 to about 100, m is from about 1 to about 40, the molecular weight of the residue $(C_2H_4O-)_x-(C_3H_6O-)_yX$ is from about 50 to about 2000, and x and y are such that the weight ratio of oxyethylene:oxypropylene is from about 100:0 to about 0:100.

2. The composition according to claim 1 wherein the dimethicone copolyol is selected from $C_{12}$ to $C_{20}$ alkyl dimethicone copolyols and mixtures thereof.

3. The composition according to claim 2 wherein the dimethicone copolyol is cetyl dimethicone copolyol.

4. The composition according to claim 1 comprising from about 0.01% to about 25% by weight of the dimethicone copolyol.

5. The composition according to claim 4 comprising from about 0.1% to about 5% by weight of the dimethicone copolyol.

6. The composition according to claim 1 wherein the ratio of the silicone surfactant to the dimethicone copolyol is from about 0.5:1 to about 15:1 by weight.

7. The composition according to claim 6 wherein the ratio of the silicone surfactant to the dimethicone copolyol is from about 1:1 to about 10:1 by weight.

8. The composition according to claim 7 wherein the ratio of the silicone surfactant to the dimethicone copolyol is from about 2:1 to about 8:1 by weight.

9. The composition according to claim 1 wherein the silicone surfactant is selected from the group consisting of dimethicone copolyols of the general formula (I) wherein the end-capping group X is methyl and y is 0, and mixtures thereof.

10. The composition according to claim 1 comprising from about 10% to about 70% by weight of a dental abrasive selected from the group consisting of silica, alumina, aluminosilicates, magnesium and zirconium silicates, calcium ortho-, pyro- meta- and polyphosphates, calcium and magnesium carbonates, insoluble metaphosphates and thermosetting polymerised resins.

11. The composition according to claim 10 comprising an amount of a fluoride ion source sufficient to provide from 50 ppm to 3500 ppm of fluoride ions.

12. The composition according to claim 1 comprising from about 0.1% to about 1% by weight of a binder.

13. The composition according to claim 1 wherein the composition further comprises an inorganic persalt bleaching agent.

14. The composition according to claim 1 wherein the molecular weight of the residue $(C_2H_4O-)_x(C_3H_6O-)_yX$ is from about 250 to about 1000.

15. The composition according to claim 1 wherein x and y are such that the weight ratio of oxyethylene:oxypropylene is from about 100:0 to about 20:80.

* * * * *